(12) United States Patent
Axelson, Jr. et al.

(10) Patent No.: US 7,666,187 B2
(45) Date of Patent: Feb. 23, 2010

(54) BONE SHAPED CUTTING BLOCK

(75) Inventors: Stuart L. Axelson, Jr., Succasunna, NJ (US); Gennaro Barile, Secaucus, NJ (US); David J. Neal, Oak Ridge, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1029 days.

(21) Appl. No.: 10/830,179

(22) Filed: Apr. 22, 2004

(65) Prior Publication Data

US 2005/0240195 A1    Oct. 27, 2005

(51) Int. Cl.
*A61B 17/58* (2006.01)
(52) U.S. Cl. .................................................. 606/88
(58) Field of Classification Search ............. 606/86–89; 623/20.14–20.36
See application file for complete search history.

(56) References Cited

U.S. PATENT DOCUMENTS

| | | | |
|---|---|---|---|
| 4,703,751 A * | 11/1987 | Pohl | 606/62 |
| 4,892,093 A * | 1/1990 | Zarnowski et al. | 606/82 |
| 5,012,909 A | 5/1991 | Machida et al. | |
| 5,129,909 A * | 7/1992 | Sutherland | 606/88 |
| 5,364,401 A | 11/1994 | Ferrante et al. | |
| 5,462,549 A * | 10/1995 | Glock | 606/86 |
| 5,490,854 A * | 2/1996 | Fisher et al. | 606/88 |
| 5,683,397 A | 11/1997 | Vendrely et al. | |
| 5,817,097 A * | 10/1998 | Howard et al. | 606/87 |
| 5,916,220 A * | 6/1999 | Masini | 606/88 |
| 6,187,010 B1 * | 2/2001 | Masini | 606/86 |
| 6,258,095 B1 | 7/2001 | Lombardo et al. | |
| 6,585,771 B1 * | 7/2003 | Buttermilch et al. | 623/22.12 |

* cited by examiner

*Primary Examiner*—Thomas C Barrett
*Assistant Examiner*—Michael J Araj
(74) *Attorney, Agent, or Firm*—Lerner, David, Littenberg, Krumholz & Mentlik, LLP

(57) ABSTRACT

A cutting block for resecting a bone, particularly the distal femur, has a body with a first generally planar bone contacting surface to contact the resected distal surface of the femur. The body has a second surface spaced from the bone contacting surface along an axis perpendicular to said generally planar bone contacting surface. The body has a perimeter surface extending between the first and second surfaces, wherein the perimeter surface is at least partially curved with respect to the axis in both a direction generally perpendicular thereto and generally parallel thereto. The perimeter surface may be polished.

9 Claims, 4 Drawing Sheets

BONE SHAPED CUTTING BLOCK

BACKGROUND OF THE INVENTION

The present invention relates generally to the implant of prosthetic joints and pertains, more specifically, to the preparation of the distal femur for the implantation of a femoral knee prosthesis, utilizing a femoral cutting guide to assist in establishing the surfaces necessary for locating and securing the prosthesis in place on the femur.

The implant of a prosthetic knee joint requires that the distal femur be prepared to receive the femoral component of the knee prosthesis by cutting the bone of the femur to establish accurately located surfaces. Upon implantation, the femoral component will rest on these surfaces. As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

Various resection guides are available to the surgeon for assisting in guiding a saw blade to make the femoral cuts which establish the desired surfaces. These guides usually have guide surfaces for making four resections and are located and secured on the distal femur, upon an already resected transverse surface on the distal femur. Typically, surfaces are provided for guiding the saw blade during the execution of an axially directed anterior femoral cut, an axially directed posterior femoral cut, an anterior chamfer and a posterior chamfer, all specifically related to the size of the femoral knee prosthesis to be implanted and to the position and orientation of the femoral knee prosthesis on the distal femur. This type of cutting block is known as a four in one cutting block. Such blocks are shown in U.S. Pat. Nos. 4,892,093, 5,012,909, 5,364,401, 5,683,397 and 6,258,095. The appropriate location of a femoral cutting guide, then, generally requires the use of well known instruments and alignment techniques to determine the size of the femoral knee prosthesis which will be implanted at an implant site in a particular recipient, and to locate the corresponding femoral cutting guide appropriately on the transverse distal femoral surface for proper placement of the femoral knee prosthesis upon implant at the implant site.

Total knee replacement surgery, according to traditional practice, requires a relatively large incision in the patient in order to realign the patient's leg, remove any diseased bone and cartilage, and provide a proper surface for engagement with the tibial and femoral prostheses which must mate to form the total knee replacement. Such large and complicated incisions increase surgical time and risk and also lengthen patient recovery. Accordingly, more recent minimally invasive techniques have become available, which greatly reduce the size of the required incision. The cutting guide of the present invention and the methods utilized in performing total knee arthroplasty using such instruments significantly reduces the amount of cutting and other disruption and damage to such soft tissue with the result of faster recovery time for the patients.

SUMMARY OF THE INVENTION

It is therefore one object of the invention to provide a femoral cutting guide for use in minimally invasive surgery (MIS) which has a shape approximating the size of the distal femur and having rounded and/or polished surfaces to eliminate any potential damage to surrounding soft tissue.

It is yet another object of the invention to provide a cutting block that has an outer perimeter which does not extend beyond the distal envelope of the femur which is being resected.

Thus, the cutting guide is contoured to match the anatomy of the bone. In the present invention, a four-in-one femoral resection guide has the approximate shape of the femur when viewed from the distal end. This includes rounded corners and no sharp edges designed to be soft tissue friendly and to fit within a minimally invasive surgery incision envelope.

The block is preferably pinned together by small diameter cylindrical pins located at the ends of the saw blade slots. The design allows the saw blade a greater degree to travel in the slot, when compared to a traditional solid sidewall construction. This is true even when compared to traditional sidewall designs that incorporate a flared out side wall. The use of pins offers a much greater degree of angular travel. Therefore, blocks can be made smaller, maintaining the same amount of bone removed. This is especially useful in MIS where space is confined.

In addition, allowing the saw blade to pivot about the pins also results in reducing the risk of burrs being created on the block. Even with chamfered or tapered out solid side wall slot edges, the prior art cutting block designs and methods of manufacture allows some degree of rolling over, as the oscillating saw comes in contact with the sides. Cylindrical pins at the ends of the cutting block slots virtually eliminates this condition.

The block is preferably made in five separate pieces spaced to form saw guide slots. Preferably the entire block is pinned and welded together. Previously, the slots were made by wire Electron Discharge Machining (EDM). The use of pinning and welding saves machine time/cost. In addition, using pins to hold the block pieces together allows the most anterior piece to be connected to the adjacent posterior piece to form the anterior saw guide slot by placing pins adjacent the outer medial and lateral sides of the cutting block. When making the anterior cut, this not only allows the saw blade to pivot within the slot around the medial and lateral pins but also helps guide the saw blade away from the collateral ligaments. Similarly, when making the anterior chamfer cut, the generally triangular middle piece of the cutting block is coupled to the adjacent anterior piece by a pin located adjacent both the medial and lateral sides of the block. Because of the rounded shape of the block, these pins may be spaced outwardly of the pins connecting the most anterior piece to its adjacent piece. The gap between the pieces guide the saw for the posterior cut. The posterior most piece of the block is connected to the adjacent anterior piece by a pair of pins centrally located between the two pieces. These pins are located centrally so that the saw is guided away from the anterior and posterior cruciate ligaments. While most femoral components currently utilized sacrifice the anterior cruciate ligament, it may be possible in the future to design implants that retain the same. As above, the triangular centerpiece is connected to the next most posterior piece by a pair of centrally located pins to form the posterior chamfer cut slot. In the preferred embodiment, these pins are extended portions of the pins between the most posterior piece and the next adjacent anterior piece.

These and other objects of the invention are achieved by a cutting block for resecting a bone, particularly the distal femur, which has a body with a first generally planar bone contacting surface for example to contact the resected distal surface of the femur. The body has a second surface spaced from the bone contacting surface along an axis perpendicular to said generally planar bone contacting surface. The body has a perimeter surface extending between the first and second surfaces, wherein the perimeter surface is at least partially curved with respect to the axis in both a direction generally perpendicular thereto and generally parallel thereto. The perimeter surface may be polished.

The cutting block body includes a plurality of slots for guiding a saw blade. Preferably, the slots are positioned so that four cuts of the femur can be made, namely anterior, posterior, anterior chamfer and posterior chamfer cuts.

The slots intersect the perimeter surface to form open or closed ends. The closed ends may be a sidewall but may be formed by pins extending from the upper or lower slot surface adjacent the open ends. The pin allows the saw blade to pivot therearound to allow a generally planar saw blade to perform a cut wider than the width of the cutting block. In addition, pins located adjacent the medial and lateral sidewalls of the block help prevent the saw blade from coming into contact with the collateral ligaments of the knee. This is particularly important when making the anterior and anterior chamfer cuts on the distal femur. Alternatively, the medial or lateral pin can be replaced with a rounded or curved wall adjacent the perimeter of the cutting block. In this case, the end of the cutting block would not be open but rather would have an outer surface continuous with the remainder of the block with the curved inner surface for contacting the edge of the planar saw blade. When making the posterior and posterior chamfer cuts, it is important to avoid having the saw blade inadvertently contact the anterior cruciate ligament or the posterior cruciate ligament. Consequently, placement of these pins centrally within the slots helps prevent such inadvertent contact. While in the preferred embodiment, the posterior and posterior chamfer slots are formed by two adjacent centrally located pins connecting adjacent pieces of the block, a single wider centrally located pin could also be utilized. However, use of two pins provides for better rotational stability between the two pieces.

At least part of the perimeter of the saw block is curved with respect to the central axis both in the plane perpendicular thereto and parallel thereto. The curve from the proximal bone contacting surface towards the distal facing second surface in a direction parallel to the central axis, at any given section, has at least one point thereon at a greater distance from the central axis than the distance to the same section along the first surface or the second surface. In other words, the medial and lateral cutting block surfaces are preferably arcuate with the largest diameter about the central axis being located intermediate to the proximal and distal surfaces of the block. Preferably, the width of the block, both in the anterior-posterior and medial-lateral directions is equal to or less than that of the corresponding dimension on the femur.

BRIEF DESCRIPTION OF THE DRAWINGS

The invention can be performed in various ways and some embodiments will now be described by way of example and with reference to the accompanying drawings in which.

DETAILED DESCRIPTION

Figure 1:
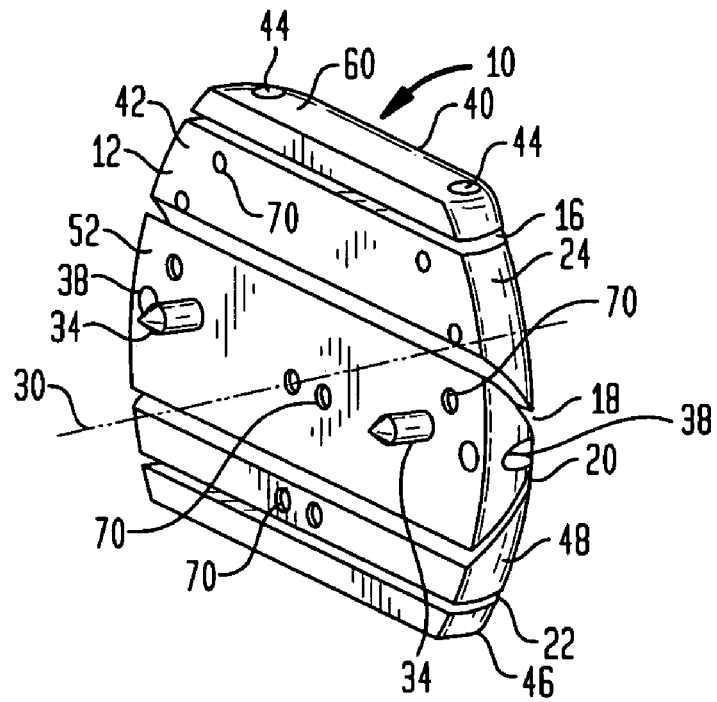
FIG. 1 is a rear isometric view of the cutting block of the present invention showing the proximal bone contacting face.
Figure 2:
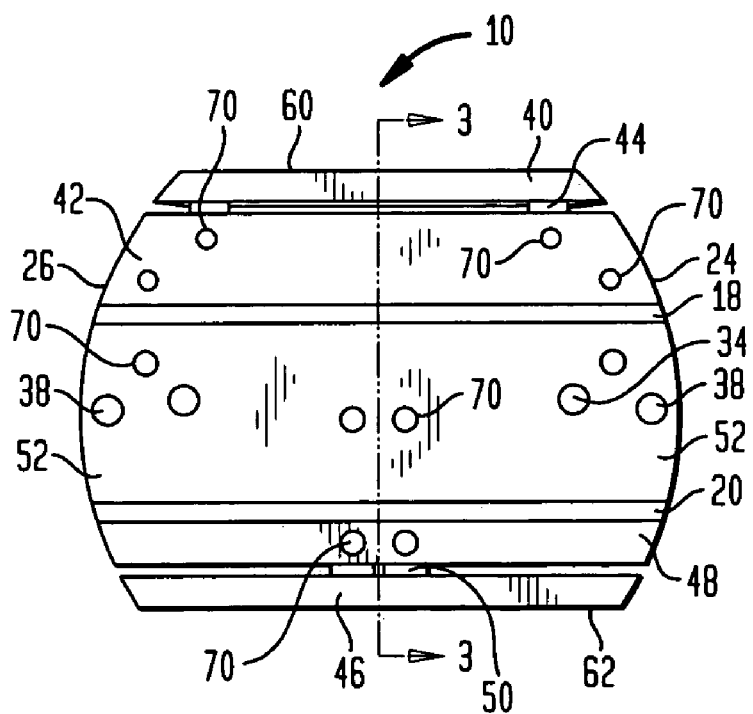
FIG. 2 is a rear view of the cutting block of FIG. 1.

Referring to the figures, there is shown a cutting block generally denoted as 10 which includes a proximal bone facing surface 12 and an opposite distal facing surface 14. While in the preferred embodiment surface 12 is flat for contacting an already resected distal femur, it is possible to mount the block to a non-resected distal femur and have surface 12 curved to match the shape of the natural condyles. In the preferred embodiment, the block includes four slots 16, 18, 20 and 22, respectively. Slot 16 is adapted to perform an anterior cut, slot 22 is adapted to perform a posterior cut, slot 18 is adapted to an anterior-chamfer cut and slot 20 is adapted to perform a posterior-chamfer cut. These guide slots are preferably used with an oscillating saw blade in a well known manner.

The cutting block includes perimeter surfaces 24 and 26 which are curved in a plane perpendicular to a central axis 30 perpendicular to the bone facing surface 12 of cutting block 10. Axis 30 is usually co-axial or parallel to the mechanical axis of the femur when the block 10 is placed on the femur. Surfaces 24, 26 may face either medially or laterally when mounted on the femur depending on whether block 10 is mounted on the left or right femur.

Figure 4:
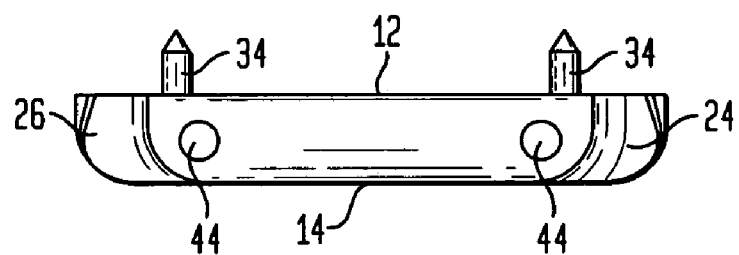
FIG. 4 is a top view of the cutting block of FIG. 2.
Figure 5:
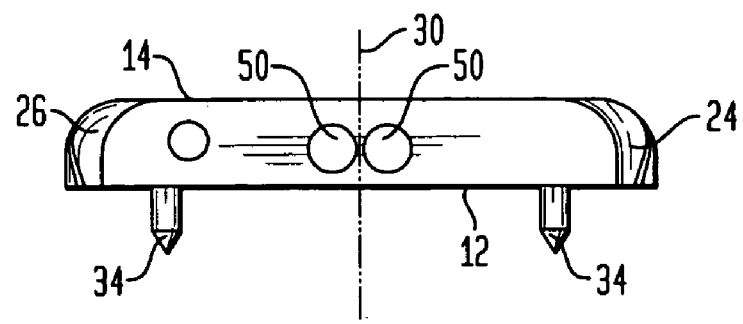
FIG. 5 is a bottom view of the cutting block of FIG. 2.

As best seen in FIGS. 4 and 5, the perimeter surfaces 24, 26 are also curved in a plane parallel to axis 30. Preferably, the maximum distance from axis 30 on each side 24, 26 is at a point thereon between surfaces 12 and 14. However, the maximum distance could be along contacting surface 12.

In the preferred embodiment, bone facing surface 12 includes pins 34 for attaching cutting block 10 to the prepared surface of a distal femur. In addition, the cutting block may include a plurality of throughbores for receiving bone pins (not shown) to fix the cutting block to the distal femur. In addition, angled holes 38 on surfaces 24, 26 may be provided to allow the use of bone pins angled in a medial or lateral direction. A provision for a handle on surface 24 and 26 may also be included.

Figure 3:
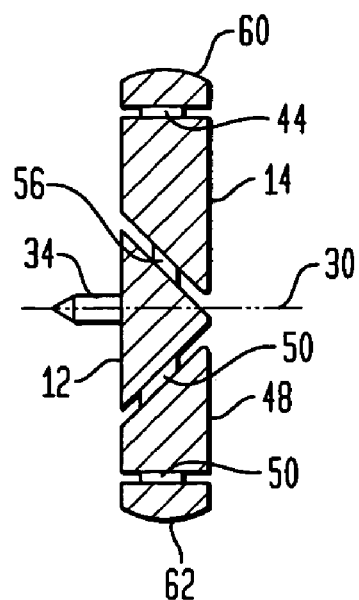
FIG. 3 is a cross-sectional view along lines 3-3 of FIG. 2.

In the preferred embodiment, block 10 is made of five parts pinned and welded together. Slot 16 is formed by an anterior block part 40 which is separated from the adjacent more posterior part 42 by distance determined by the thickness of the saw blade. In the preferred embodiment, part 40 is pinned to part 42 by a pair of pins 44 which, as can be seen in FIG. 3, have a diameter less than the thickness of the cutting block between surfaces 12 and 14 and located adjacent the medial and lateral ends of slot 18. These pins are preferably located adjacent the medial and lateral sides of the block to prevent inadvertent contact between the saw blade and the collateral ligaments. Similarly, the posterior most part 46 of the cutting block 10 is pinned in a similar manner to the next most anterior part 48 by two pins 50 which can be seen in FIGS. 2, 3, 5 and 8. Pins 44 and 50 are shown in phantom since their outer ends are preferably welded and polished so they blend into the top and bottom surfaces of cutting block 10.

Figure 8:
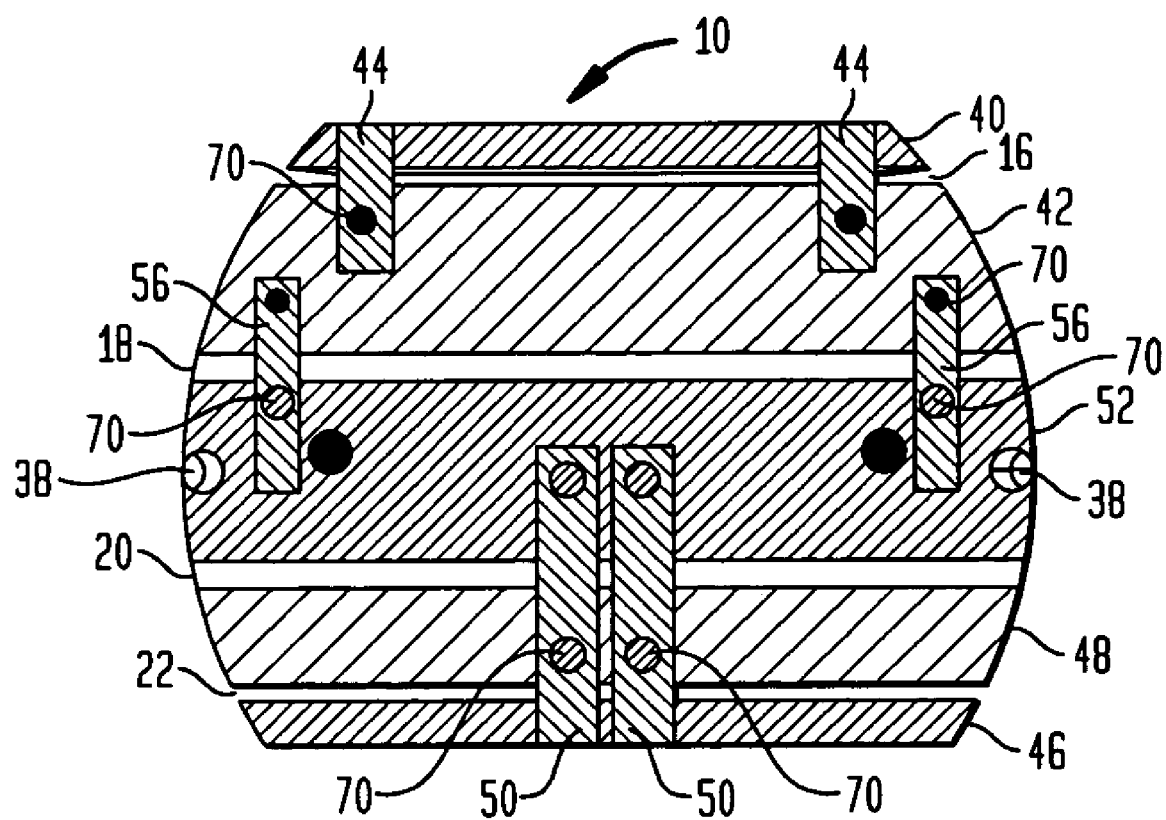
FIG. 8 is a cross-sectional view along lines 8-8 of FIG. 7.

Pins 50 are centrally located with respect to slot 22 in order to avoid inadvertent contact between the saw blade and the anterior cruciate ligament or the posterior cruciate ligament. In the preferred embodiment, pins 50 extend all the way through part 48 and into triangular part 52 thereby coupling parts 46, 48 and 52 together and create the saw blade slots 20 and 22. Part 52 is coupled to the next most anterior part 42 by a pair of pins 56 which are located adjacent the medial and lateral ends of slot 18. Note that in the preferred embodiment, as shown in FIG. 8, pins 44 and 56 are separate pins since extending pins 44 through part 42 into part 52 would result in the pins being more centrally located than their desired position adjacent the medial and lateral ends of slots 18.

Preferably, the outer ends of pins 44 and 50 connecting parts 40, 42, 46, 48 and 52 are welded to the piece in which they are received. The outwardly facing welded surfaces of pins 44 and 50 are then ground smooth with the top surface 60 and the bottom surface 62 of the cutting block. In the preferred embodiment, the pins are also connected to block pieces 40, 42, 46, 48 and 52 by a cross-pin 70 which is inserted into cross-bores in each block piece. During assembly, for example, pin 44 is located in a bore in piece 42 and a cross-bore is made perpendicular to the axis of the bore receiving pin 44. This bore is drilled through piece 42 into the pin 44 and a small cross-pin 70 is inserted into the bore in both piece 42 and pin 44. This ensures that the width of slot 16 is fixed. The outer surface of piece 42 including pin 70 is then welded in the area of the bore to ensure that the pin does not back out. Again, the surfaces around pins 70 are ground or machined flush with the adjacent surface, which, in the preferred embodiment, is bone contacting surface 12. The other pins 44 as well as pins 50 and 56 are fixed to the respective pieces 42, 48 and 52 in a similar manner. This ensures that once assembled, the pieces of the block cannot be either disassembled or moved out of proper alignment.

In the preferred embodiment, upper and lower anterior and posterior facing surfaces 60 and 62 are preferably curved in a manner similar to that of perimeter surfaces 24, 26. However, these surfaces could also be flat. In the preferred embodiment, all or some of these surfaces 24, 26, 60, 62 may be polished.

Figure 6:
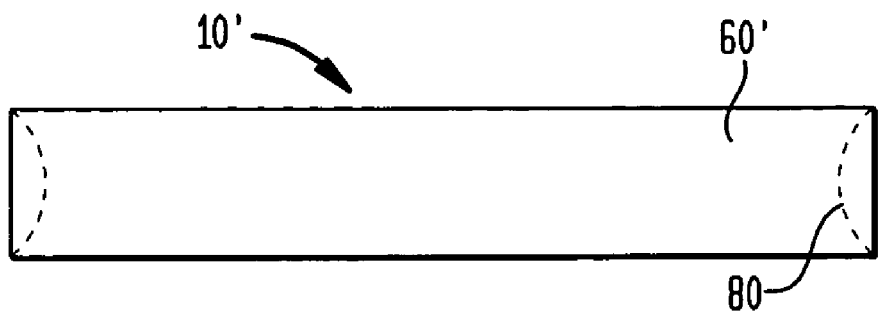
FIG. 6 is a top view of a cutting block having arcuate inwardly facing end walls.
Figure 7:
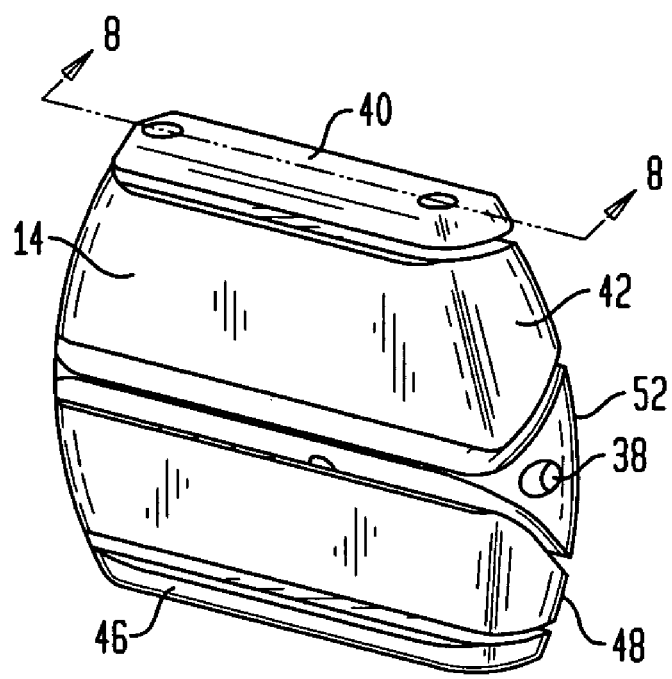
FIG. 7 is a front isometric view of the cutting block of the present invention.

FIG. 6 shows a top view of cutting block 10' having a top surface 60' and a saw blade slot having arcuate inwardly facing end walls 80.

In use, block 10 is placed against the already resected distal surface of the femur. After making the distal femoral cut in a routine manner, block 10 is then mounted on the prepared surface of the femur by inserting pins 34 into the exposed cancellous bone of the femoral condyles. Bone pins (not shown) may be inserted through holes 38 for positive fixation. The anterior and posterior cuts are then made by inserting an oscillating saw blade into slots 16, 22, respectively. The edges of the saw blade can contact pins 44, and 50, respectively to allow the blade to pivot in a wide arc to ensure that all of the bone is resected. As discussed above, the reason that pins 44 and 56 are located adjacent the outer open end of slots 16 and 18 and pins 50 are located centrally within slots 20 and 22, thereby allowing the ends of slots 20 and 22 to be open, is to help prevent the inadvertent contact between the collateral ligaments (slots 16 and 18), anterior cruciate ligament and posterior cruciate ligament with the saw blade.

After the anterior and posterior cuts are made, then the chamfer cuts may then be made with a cutting block using slots 18 and 20. The surgeon may choose to perform the four cuts in any other desired sequence.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cutting block for resecting a bone comprising:
a body having a first generally planar bone contacting surface and a second surface spaced from said bone contacting surface along first axis perpendicular to said generally planar bone contacting surface;
said body having a perimeter surface extending between said first and second surfaces, at least a medial and a lateral perimeter surface of the body curved along a plane parallel to the planar bone contacting surface and along a plane perpendicular to the bone contacting surface, wherein said body is to be used to resect a distal femur and includes a plurality of slots for guiding a saw blade, wherein at least one of the slots includes two inwardly facing end surfaces extending from a bottom slot surface to a top slot surface at a location adjacent said perimeter surface of said body and wherein the inwardly facing end surfaces of said slot are curved surfaces, each curved surface having a central longitudinal axis extending in a direction from a top surface and a bottom surface of the body, parallel to the bone contacting surface which top and bottom surfaces connect ends of the medial and lateral perimeter surfaces and each inwardly facing curved surface extending toward a center of the top and bottom surfaces of said body located between the medial and lateral perimeter surfaces, the inwardly facing curved surface for engaging an edge of the saw blade.

2. The cutting block as set forth in claim 1 wherein said end surface is formed by a cylindrical pin.

3. The cutting block as set forth in claim 2 wherein said perimeter surface is polished.

4. A cutting block for resecting a distal femur comprising:
a body having a width in a medial-lateral direction and height in an anterior-posterior direction and a proximally facing bone contacting surface and a distally facing surface opposite said proximal surface, said proximal and distal surfaces spaced along a central axis extending in an anterior- posterior direction, said body having a medial and lateral perimeters extending between said proximal and distal surfaces wherein at least part of each of said perimeters is at a greater distance from said central axis than said medial and lateral perimeter at said proximal and distal surfaces and wherein the body has a width less than or equal to the medial-lateral dimension of the femur throughout the height of the block and a height less than or equal to the anterior-posterior dimension of the femur throughout the width of the block wherein said body includes a plurality of slots for guiding a saw blade used to make an anterior cut, a posterior cut, an anterior chamfer cut and a posterior chamfer cut on the distal femur, wherein said slots for said anterior cuts include an inwardly facing end surface extending from a bottom slot surface to a top slot surface at a location adjacent said perimeter surface of said body, wherein said end surface has an arcuate portion extending towards the central axis of said body for engaging an edge of the saw blade, and wherein said end surface is formed by a cylindrical pin, the cylindrical pin having a longitudinal axis extending parallel to the central axis.

5. The cutting block as set forth in claim 4 wherein said medial and lateral perimeter surface is polished.

6. The cutting block as set forth in claim 4 wherein said slots for said posterior and posterior chamfer cuts intersect said perimeter surface to form an open end.

7. The cutting block as set forth in claim 6 wherein the slot for the posterior cut further includes at least one pin extending from a bottom to a top surface of said slot, said pin adjacent a center of said slot and having a rounded outer surface for engaging the saw blade.

8. A cutting block for resecting bone comprising:
a body having a first generally planar bone contacting surface and a second surface spaced from said bone contacting surface along an axis perpendicular to said generally planar bone contacting surface;
said body having a perimeter surface extending between said first and second surfaces, said perimeter surface at least partially curved with respect to said axis in both a direction generally perpendicular thereto and generally parallel thereto, wherein said body is to be used to resect a distal femur and includes a plurality of slots for guiding a saw blade, wherein at least one of said slots includes an inwardly facing end surface extending from a bottom slot surface to a top slot surface at a location adjacent said perimeter surface of said body, an end surface of said slot has an arcuate portion extending towards a center of said body for engaging an edge of the saw blade, and wherein said end surface is formed by a cylindrical pin having a longitudinal axis extending parallel to the generally planar bone contacting surface in an anterior-posterior direction.

9. A cutting block for resecting a distal femur comprising:
a body having a width in a medial-lateral direction and height in an anterior-posterior direction and a proximally facing bone contacting surface and a distally facing surface opposite said proximal surface, said proximal and distal surfaces spaced along a central axis, said body having a medial and lateral perimeters extending between said proximal and distal surfaces wherein at least part of each of said perimeters is at a greater distance from said central axis than said medial and lateral perimeter at said proximal and distal surfaces and wherein the body has a width less than or equal to the medial-lateral dimension of the femur throughout the height of the block and a height less than or equal to the anterior-posterior dimension of the femur throughout the width of the block wherein said body includes a plurality of slots for guiding a saw blade used to make an anterior cut, a posterior cut, an anterior chamfer cut and a posterior chamfer cut on the distal femur, wherein said slots for said anterior cuts include an inwardly facing end surface extending from a bottom slot surface to a top slot surface at a location adjacent said perimeter surface of said body, wherein said end surface has an arcuate portion extending towards a center of said body for engaging an edge of the saw blade, and wherein said end surface is formed by a cylindrical pin wherein said slots for said posterior and posterior chamfer cuts intersect said perimeter surface to form an open end wherein the slot for the posterior cut further includes at least one pin extending from a bottom to a top surface of said slot, said pin adjacent a center of said slot and having a rounded outer surface for engaging the saw blade.

* * * * *